(12) United States Patent  
Liphardt

(10) Patent No.: US 7,965,390 B1  
(45) Date of Patent: Jun. 21, 2011

(54) AUTOMATIC SAMPLE ALIGNMENT SYSTEM AND METHOD OF USE

(75) Inventor: Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 312 days.

(21) Appl. No.: 12/378,019

(22) Filed: Feb. 10, 2009

Related U.S. Application Data

(60) Provisional application No. 61/065,255, filed on Feb. 11, 2008.

(51) Int. Cl.
*G01B 11/00* (2006.01)
*G01J 4/00* (2006.01)
*G01N 21/55* (2006.01)

(52) U.S. Cl. ........ 356/399; 356/445; 356/369; 356/364; 356/400

(58) Field of Classification Search .................. 356/445, 356/364, 369, 399, 400
See application file for complete search history.

(56) References Cited

U.S. PATENT DOCUMENTS

| | | | |
|---|---|---|---|
| 6,744,510 B2 * | 6/2004 | Gweon et al. | 356/369 |
| 6,969,862 B2 * | 11/2005 | Muraki et al. | 250/492.22 |
| 7,084,978 B1 | 8/2006 | Liphardt | 356/364 |
| 7,136,172 B1 * | 11/2006 | Johs et al. | 356/614 |
| 7,230,699 B1 | 6/2007 | Liphardt et al. | 356/364 |
| 7,277,171 B1 | 10/2007 | Johs et al. | 356/369 |
| 7,304,737 B1 | 12/2007 | Liphardt et al. | 356/369 |
| 7,304,792 B1 | 12/2007 | Liphardt et al. | 359/385 |
| 2010/0220330 A1 * | 9/2010 | Ran et al. | 356/445 |

* cited by examiner

*Primary Examiner* — L. G Lauchman
(74) *Attorney, Agent, or Firm* — James D. Welch

(57) ABSTRACT

A system which automatically reduces change in effective angle and plane of incidence of a reflected focused beam of electromagnetic radiation entering a detector, via use of a detector with dimensions less than is the spatial spread of a reflected focused beam at a location distal to the location on said sample from which it is caused to reflect, preferably after passing through a collimating lens. The basis of operation is that the portion of a reflected focused beam intercepted by the detector changes with change in sample position and/or orientation.

11 Claims, 4 Drawing Sheets

AUTOMATIC SAMPLE ALIGNMENT SYSTEM AND METHOD OF USE

CROSS-CORRELATION TO PRIOR APPLICATIONS

This application Claims Benefit of Provisional Application Ser. No. 61/065,225 Filed Feb. 11, 2008.

TECHNICAL FIELD

The present invention relates to systems for aligning samples so that change in angle, and plane, of a reflection of a focused beam of electromagnetic radiation impinged on a sample are reduced, when sample orientation changes. More particularly the present invention is a system which automatically achieves the desired effect via use of a detector with dimensions less than is the spatial spread of said reflected focused beam, at a location distal to the location on said sample from which it is caused to reflect. The basis of operation is that the portion of a reflected focused beam intercepted by the detector changes with change in sample orientation. A preferred embodiment provides a collimating lens prior to the detector.

BACKGROUND

In the practice of reflectometry, ellipsometry, polarimetry and the like, it is critically important to know the precise angle (AOI), and plane (POI), of incidence at which a beam of electromagnetic radiation is caused to impinge upon a sample, to allow accurate determination of values of sample characterizing parameters, such as the PSI and DELTA thereof. Further, it is noted that the (AOI) and (POI) can change with location on a sample surface as the result of said surface being uneven, thereby requiring alignment at each location of a sample surface investigated. Relative translation between a sample and a reflectometer, ellipsometer or polarimeter can cause an effective sample (AOI) or (POI) orientation change.

Examples of systems which are applicable to effecting sample alignment are disclosed in, patents to Liphardt and Liphardt et al. U.S. Pat. Nos. 7,084,978; 7,230,699; 7,304,792; 7,304,737; and to Johs et al. U.S. Pat. No. 7,277,171. In general, prior art systems provide means for adjusting the orientation of a sample to cause a known, precise angle (AOI) and plane (POI) of incidence.

In view of the above, it should be apparent that a system that reduces the necessity of sample alignment after an initial alignment procedure is performed, would be of benefit and provide utility. In particular, such a system would reduce researcher need to adjust for small changes in (AOI) and (POI) resulting from lateral shifts, or rotation of the a sample, after an initial alignment procedure is performed.

DISCLOSURE OF THE INVENTION

The present invention comprises a system which automatically reduces change in alignment of angle and plane of incidence of a focused beam of electromagnetic radiation which is caused to impinge on a sample which reflects therefrom, and sequentially comprises:
 a source of beam of electromagnetic radiation;
 a focusing lens;
 a sample; and
 a detector.

It is noted that a preferred embodiment further comprises a collimating lens before said detector, which serves to provide collimated electromagnetic radiation thereinto.

The basis of operation of the present invention system is that said detector has dimensions less than is the spread of said expanding focused beam at least one location distal to the location on said sample from which it is caused to reflect. In use said source of beam of electromagnetic radiation is caused to direct a beam of electromagnetic radiation through said focusing lens such that the resulting focused beam reflects from said sample in an expanding beam manner, and said detector is positioned at a location to intercept less than the entire expanding reflected beam at the location of said detector, preferably via a collimating lens. The invention is found in the positioning of the detector in said expanding beam which reflected from said sample, such that the size of said detector is less than that of said expanding beam at the location whereat said detector is located. The beneficial result is that the actual (AOI) and/or (POI) of the incident beam onto said sample can be changed with a lessened effect on (AOI) and/or (POI) of the reflected beam entering the detector, because different components of said reflected beam enter the detector after, as compared to before the actual incident (AOI) and/or (POI), is changed.

A preferred system which automatically preserves alignment of angle and plane of incidence of a focused beam of electromagnetic radiation which is caused to impinge on a sample which reflects therefrom, sequentially comprises:
 a source of beam of electromagnetic radiation;
 a focusing lens;
 a sample;
 a collimating lens; and
 a detector.

Again, the basis of operation is that said detector has dimensions less than is the spread of said reflected focused beam at least one location distal to the location on said sample from which it is caused to reflect, after it passes through the collimating lens. In use said source of beam of electromagnetic radiation is caused to direct a beam of electromagnetic radiation through said focusing lens such that the resulting focused beam reflects from said sample in an expanding beam manner. The collimating lens then collimates the electromagnetic radiation entering said detector, which detector is positioned at a location to intercept less than the entire collimated beam at the location of said detector. The invention is found in the size of said detector being less than that of said collimated beam at the location whereat said detector is located in said collimated beam, and the beneficial result is that the actual (AOI) and/or (POI) of the incident beam onto said sample can be changed with a lessened change in effective (AOI) and/or (POI) of the reflected beam entering the detector.

Said system can further comprises a polarizer before said sample and an analyzer thereafter, in which case said system is an ellipsometer or polarimeter.

To help with understanding it is noted that the actual (AOI) and (POI) can be best understood as being angles between the center of an incident beam of electromagnetic radiation, and a normal to the sample surface. Sample translation and/or rotation orientation changes causes said actual (AOI) and (POI) to change, but with reduced effects on the effective (AOI) and (POI) entering the detector, because different portions of the reflected beam enter thereinto.

A present invention method comprises the steps of:
 a) providing a system which automatically reduces change in angle and plane of incidence of a focused beam of electromagnetic radiation which is caused to impinge on a sample which reflects therefrom comprising:

a source of beam of electromagnetic radiation;
a focusing lens;
a sample; and
a detector;
as describe above;

b) while detecting a portion of the beam reflected from said sample causing the (AOI) and/or the (POI) of said incident beam with respect to said sample to change, and thereafter detecting a different portion of the beam reflected from said sample, without changing the position of said detector; wherein change in the effective (AOI) and (POI) of said beam detected by the detector both before and after the incident (AOI) and/or the (POI) of said incident beam with respect to said sample is caused to change, is reduced over what it would be if the detector intercepted the entire beam.

It is noted that the actual incident (AOI) and/or the (POI) of said incident beam with respect to said sample can be caused to change by lateral motion of said sample and/or by a rotation motion of said sample or other sample motion.

The present invention will be better understood by reference to the Detailed Description of this Specification, with reference to the Drawings.

DETAILED DESCRIPTION

Figure 1:
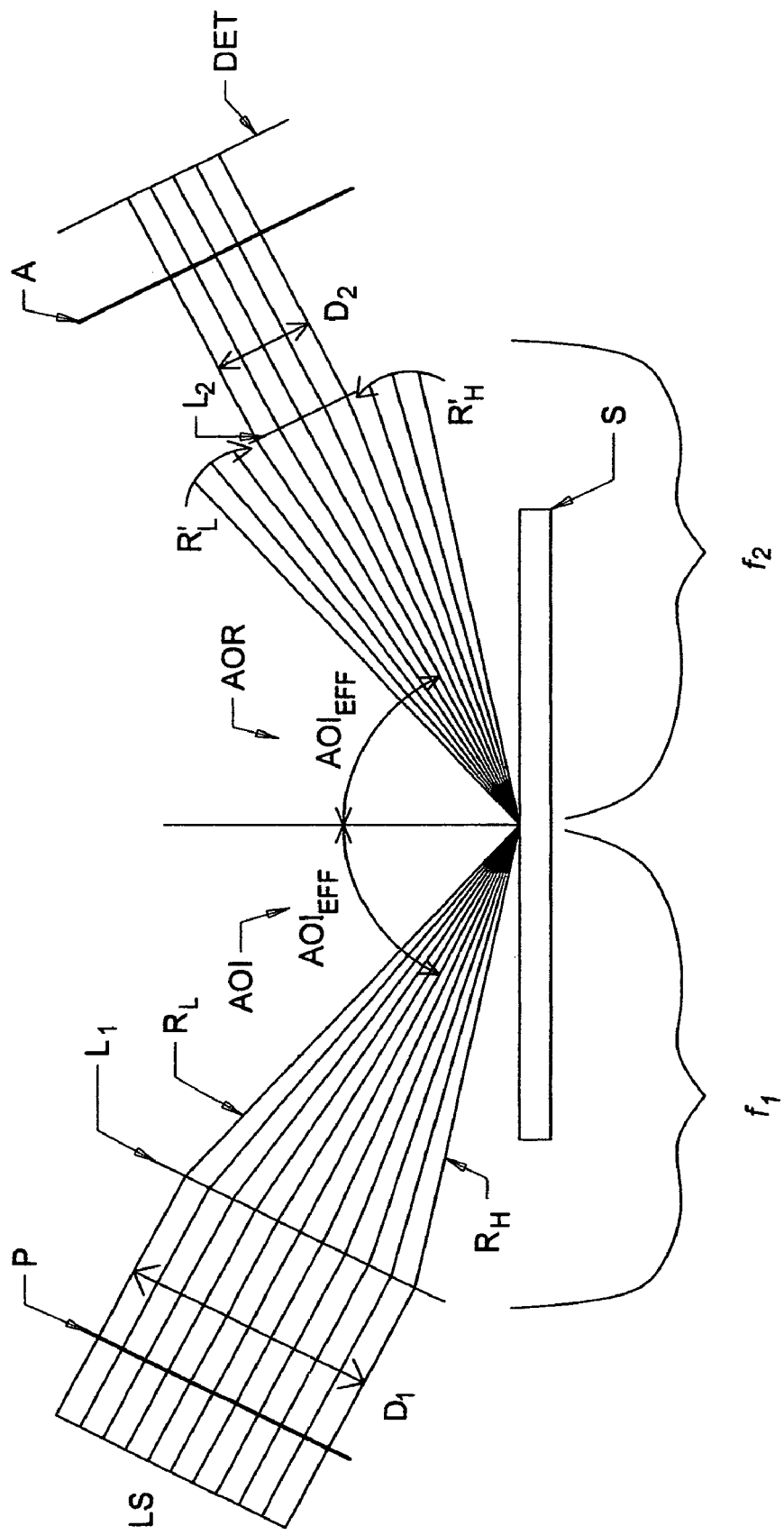
FIG. 1 shows a side elevations view of a present invention system with a sample in a first orientation and with a given angle of incidence (AOI).
Figure 2:
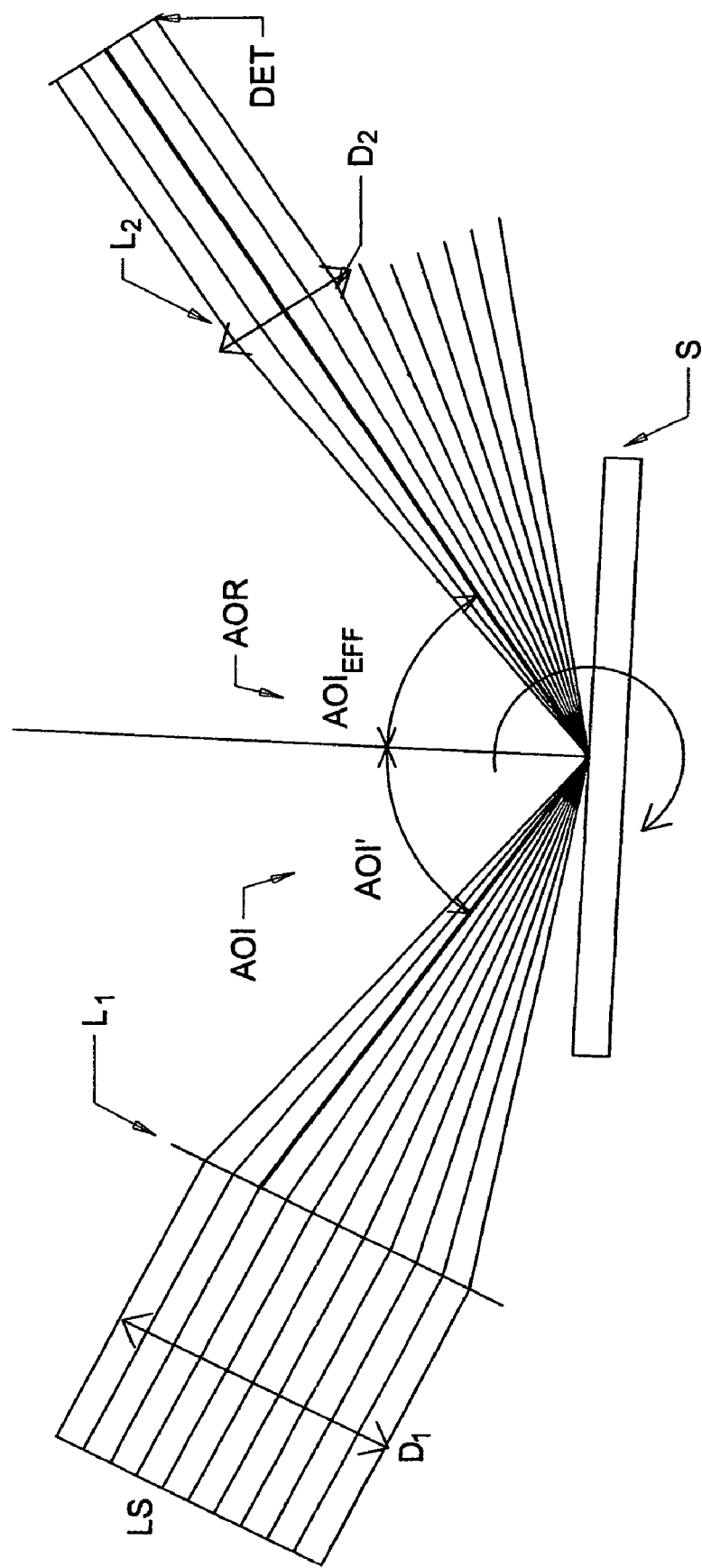
FIG. 2 shows a side elevations view of a present invention system with a sample in a second orientation and with a given angle of incidence (AOI).

Turning now the Drawings, FIG. 1 shows a side elevational view of a present invention system with a Sample (S) in a first orientation and with a given angle of incidence (AOIeff) of the incident beam to said Sample (S). Note the sequential presence of a Source (LS) of a beam of electromagnetic, a Focusing Lens (L1), a Sample (S) and a Detector (DET), preferable preceded by Collimating lens (L2). Note that the Angle of Reflection (AOR) is also (AOIeff) in FIG. 1. FIG. 2 shows a side elevational view of the same system, but in which the incident beam approaches the Sample (S) along a different, second, Angle of Incidence (AOI') orientation as the Sample (S) is indicated to have been rotated. Note, however, that the Detector (DET) intercepts different portions of the reflected beams in FIGS. 1 and 2 respectively, and that causes the "Effective" Angles of Reflection to be (AOIeff) in both FIGS. 1 and 2, which are more equal to one another than they would be if the entire beam were intercepted by the Detector (DET). That is, the Sample (S) can be rotated as indicated in FIG. 2 so that the FIG. 1 actual Angle of incidence (AOIeff) changes to (AOI') in FIG. 2, but the present invention effect of intercepting different components of the reflected beam as indicated by a comparison of FIGS. 1 and 2, causes change in the Effective Angle of Reflection or from (AOIeff) to (AOIeff') entering the Detector (DET) to be reduced. That is, while not exactly the same, comparing the FIG. 1 (AOIeff) at the Detector (DET) to (AOIeff') in FIG. 2, it will be found to be less affected than would be the case in the entire beam were intercepted by the Detector (DET). This is significant as it reduces the necessity of realigning the system whenever a Sample (S) undergoes small positioning and/or orientation changes.

Continuing, it is noted that an initial calibration step which sets the initial (AOIeff) must be carried out, but thereafter, for a range of beam (AOI's) with respect to said Sample (S), change in the (AOR's) at the Detector (DET) will be reduced, compared to (AOIeff), when Sample (S) position and/or orientation change occurs. The range of (AOI's) is determined by the relative size of the Detector (DET) as compared to the reflected beam size at the location therein where the Detector (DET) is positioned. Importantly, note also, the Detector (DET) position is not changed between the conditions shown in FIGS. 1 and 2.

Figure 3:
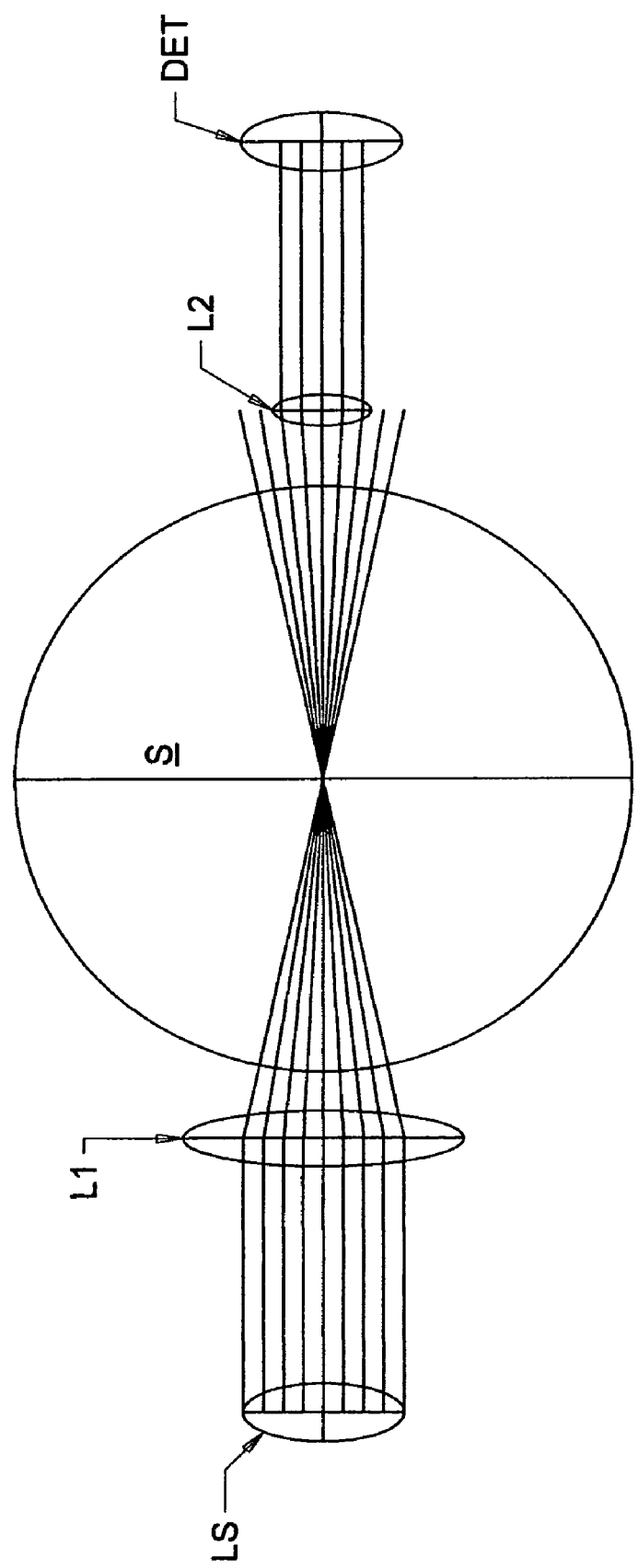
FIG. 3 shows a top view of a present invention system with a sample in a first orientation and with a given plane of incidence (POI).
Figure 4:
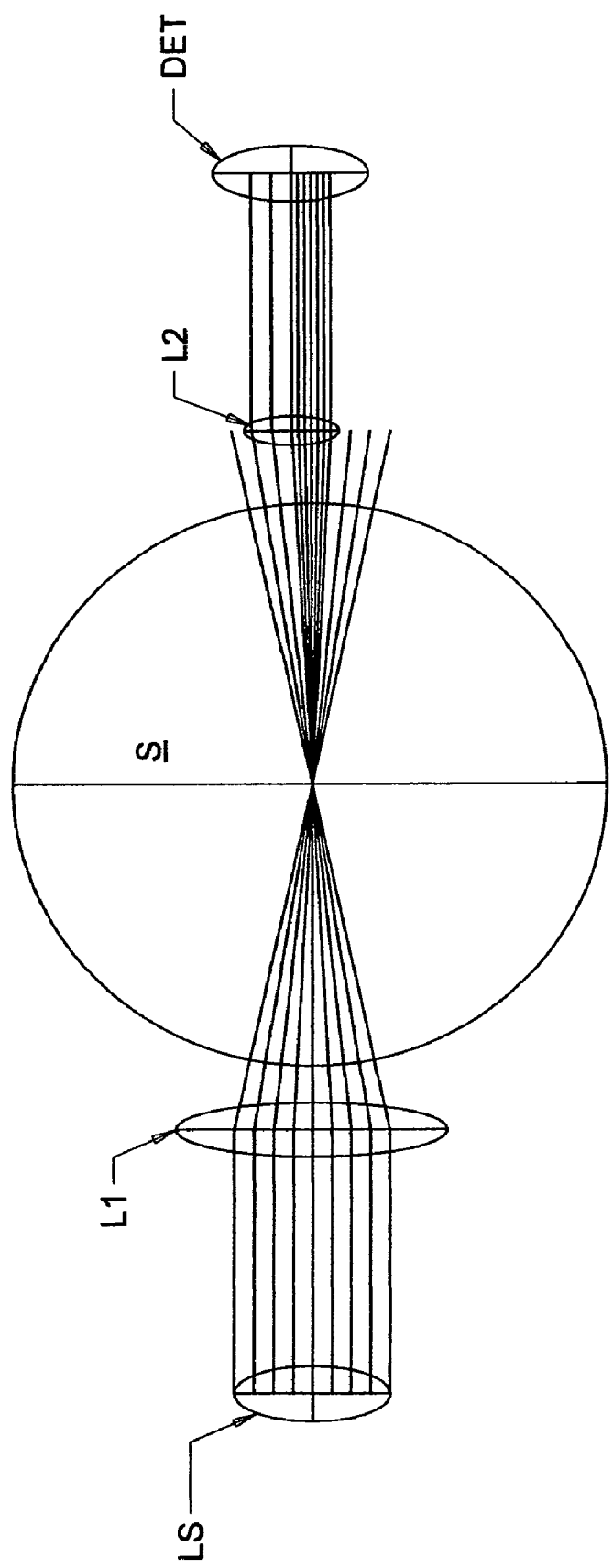
FIG. 4 shows a top elevations view of a present invention system with a sample in a second orientation and with a given plane of incidence (POI).

FIGS. 3 and 4 are included to show top views of a present invention system with a Sample (S) in a first and second orientations, to provide different planes of incidence (POI), respectively. The same effect of intercepting different components of the reflected beam in FIGS. 3 and 4, leads to a similar result as for the FIGS. 1 and 2 (AOI), but as regards the Plane of Incidence (POI). That is, in FIGS. 3 and 4 the Sample (S) can be rotated about a horizontal axis, and the Detector (DET) will continue to intercept a (POIeff) within a range of (POI's) which is determined by the relative size of the Detector (DET), as compared to the reflected beam size at the location therein where the Detector (DET) is positioned. Note again, that, importantly, the Detector (DET) position is not changed between the conditions shown in FIGS. 1 and 2.

Shown on FIG. 1 is indication of Polarizer (P) and Analyzer (A) to indicate that, while not a necessary limitation thereof, the present invention system can be an ellipsometer or polarimeter or the like system.

Finally, it is to be appreciated that a criteria is preferrably met for the present invention to optimally operate is that, as indicated on FIG. 1, the Diameter (D1) of the incident beam divide by the Focal Length of the Focusing Lens (L1) must be equal to the Diameter (D2) of the portion of the reflected beam detected by the Detector (DET) divided by the Focal Length of the Collimating Lens (L2). That is:

$$(D2/f2)<(D1/f1).$$

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A system which automatically reduces change in alignment of angle and plane of incidence of a focused beam of electromagnetic radiation which is caused to impinge on a sample and which reflects therefrom, sequentially comprising:

a source of beam of electromagnetic radiation;
a focusing lens;
a sample; and
a detector;
wherein said detector has dimensions less than is the spread of said focused beam at least one location distal to the location on said sample from which it is caused to reflect:
such that in use said source of beam of electromagnetic radiation is caused to direct a beam of electromagnetic radiation through said focusing lens such that the resulting focused beam reflects from said sample in an expanding beam manner, and wherein said detector is positioned at a location to intercept less than the entire expanding reflected beam at the location of said detector;

wherein the improvement is found in the positioning of the detector in said expanding beam which is reflected from said sample, such that the size of said detector is less that that of said expanding beam at the location whereat said detector is located;

such that the effect of a change in the angle-of-incidence and/or plane-of-incidence of the incident beam onto said sample on detector output is reduced, as compared to the change that would occur if the entire reflected beam were intercepted by the detector.

2. A system as in claim 1 which further comprises a collimating lens prior to said detector.

3. A system as in claim 1 which further comprises a polarizer before said sample and an analyzer thereafter, and in which said system is an ellipsometer or polarimeter.

4. A system which automatically reduces change in alignment of angle and plane of incidence of a focused beam of electromagnetic radiation which is caused to impinge on a sample and which reflects therefrom, sequentially comprising:
   a source of beam of electromagnetic radiation;
   a focusing lens;
   a sample;
   a collimating lens; and
   a detector;
wherein said detector has dimensions less than is the spread of said focused beam at least one location distal to the location on said sample from which it is caused to reflect, after passing through said collimating lens:

such that in use said source of beam of electromagnetic radiation is caused to direct a beam of electromagnetic radiation through said focusing lens such that the resulting focused beam reflects from said sample in an expanding beam manner, and wherein said collimating lens collimates the electromagnetic radiation entering said detector, which detector is positioned at a location to intercept less than the entire collimated beam at the location of said detector;

wherein the improvement is found in the size of said detector being less that that of said collimated beam at the location whereat said detector is located in said collimated beam;

such that the effect of a change in the angle-of-incidence and/or plane-of-incidence of the incident beam onto said sample on detector output is reduced, as compared to the change that would occur if the entire reflected beam were intercepted by the detector.

5. A system as in claim 2 which further comprises a polarizer before said sample and an analyzer thereafter, and in which said system is an ellipsometer or polarimeter.

6. A method of reducing the effects of change in angle-of-incidence and/or plane-of-incidence of a beam of electromagnetic radiation applied to investigate a sample in an ellipsometer, polarimeter or reflectometer, comprising the steps of:
   a) providing a system which automatically reduces change in alignment of angle and plane of incidence of a focused beam of electromagnetic radiation which is caused to impinge on a sample and which reflects therefrom, sequentially comprising:
      a source of beam of electromagnetic radiation;
      a focusing lens;
      a sample;
      a detector;
wherein said detector has dimensions less than is the spread of said incident focused beam at least one location distal to the location on said sample from which it is caused to reflect, after passing through said collimating lens;

such that in use said source of beam of electromagnetic radiation is caused to direct a beam of electromagnetic radiation through said focusing lens such that the resulting focused beam reflects from said sample in an expanding beam manner;

wherein the improvement is found in the positioning of the detector in said expanding beam which reflected from said sample, such that the size of said detector is less that that of said expanding beam at the location whereat said detector is located;

such that the effect of change in the angle-of-incidence and/or plane-of-incidence of the incident beam onto said sample on detector output is reduced when change in the angle-of-incidence and/or plane-of-incidence causes change in of the reflected beam entering the detector;
   b) while detecting a portion of the beam reflected from said sample causing the angle-of-incidence and/or the plane-of-incidence of said incident beam with respect to said sample to change, and thereafter detecting a different portion of the beam reflected from said sample, without changing the position of said detector.

7. A method as in claim 6 wherein the angle-of-incidence and/or the plane-of-incidence of said incident beam with respect to said sample is caused to change by lateral motion of said sample and said sample has a non-uniform surface.

8. A method as in claim 6 wherein the incident angle-of-incidence and/or the plane-of-incidence of said incident beam with respect to said sample is caused to change by a rotation motion of said sample.

9. A method of reducing the effects of change in angle-of-incidence and/or plane-of-incidence of a beam of electromagnetic radiation applied to investigate a sample in an ellipsometer, polarimeter or reflectometer, comprising the steps of:
   a) providing a system which automatically reduces change in alignment of angle and plane of incidence of a focused beam of electromagnetic radiation which is caused to impinge on a sample and which reflects therefrom, sequentially comprising:
      a source of beam of electromagnetic radiation;
      a focusing lens;
      a sample;
      a collimating lens; and
      a detector;
wherein said detector has dimensions less than is the spread of said incident focused beam at least one location distal to the location on said sample from which it is caused to reflect, after passing through said collimating lens;

such that in use said source of beam of electromagnetic radiation is caused to direct a beam of electromagnetic radiation through said focusing lens such that the resulting focused beam reflects from said sample in an expanding beam manner, and wherein said collimating lens collimates the electromagnetic radiation entering said detector;

wherein the improvement is found in the size of said detector being less that that of said collimated beam at the location whereat said detector is located in said collimated beam;

such that the effect of change in the angle-of-incidence and/or plane-of-incidence of the incident beam onto said sample on detector output is reduced when change in the angle-of-incidence and/or plane-of-incidence causes change in the reflected beam entering the detector;
   b) while detecting a portion of the collimated beam entering said detector causing the angle-of-incidence and/or the plane-of-incidence of said incident beam with respect to said sample to change, and thereafter detecting a different portion of the collimated beam entering said detector, without changing the position of said detector.

10. A method as in claim 9 wherein the angle-of-incidence and/or the plane-of-incidence of said incident beam with respect to said sample is caused to change by lateral motion of said sample and said sample has a non-uniform surface.

11. A method as in claim 9 wherein the incident angle-of-incidence and/or the plane-of-incidence of said incident beam with respect to said sample is caused to change by a rotation motion of said sample.

* * * * *